United States Patent [19]

Luomanen

[11] 4,198,970
[45] Apr. 22, 1980

[54] AIRWAY FOR DRAINAGE OF THE NASOPHARYNX

[76] Inventor: Raymond Luomanen, 544 Bay Ridge Pkwy., Brooklyn, N.Y. 11209

[21] Appl. No.: 941,259

[22] Filed: Sep. 11, 1978

[51] Int. Cl.² ................. A61M 15/00; A61M 15/06
[52] U.S. Cl. .................................................. 128/207.15
[58] Field of Search ............... 128/208, 351, DIG. 26, 128/348, 350 R

[56] References Cited

U.S. PATENT DOCUMENTS

| | | | |
|---|---|---|---|
| 1,498,810 | 6/1924 | Poe | 128/208 |
| 2,599,521 | 6/1952 | Berman | 128/208 |
| 2,705,959 | 4/1955 | Elmore | 128/351 |
| 3,306,298 | 2/1967 | Raimo | 128/351 |
| 3,568,680 | 3/1971 | Raimo | 128/351 |
| 3,756,244 | 9/1973 | Kinnear et al. | 128/351 |
| 3,774,616 | 11/1973 | White et al. | 128/351 |
| 3,908,665 | 9/1975 | Moses | 128/351 |
| 3,926,196 | 12/1975 | Bornhorst et al. | 128/351 |
| 4,054,135 | 10/1977 | Berman | 128/208 |

Primary Examiner—Robert W. Michell
Assistant Examiner—Jeffrey W. Tayon
Attorney, Agent, or Firm—Hubbell, Cohen, Stiefel & Gross

[57] ABSTRACT

An airway for insertion into the mouth and pharynx for assisting intubation comprising an elongate body having a straight section joined to a curved section and a face plate secured to the straight section at its free end. The body of the airway has an elongate U-shaped central channel open at the top and a pair of elongate open-sided U-shaped channels on either side of the central channel. The upper defining wall of one of the open-sided channels has an opening therein through which a tubular member inserted in the channel may be guided for accommodating suctioning of the nasopharynx. A tubular member may be intubated in the other side channel for simultaneously suctioning the hypopharynx.

3 Claims, 5 Drawing Figures

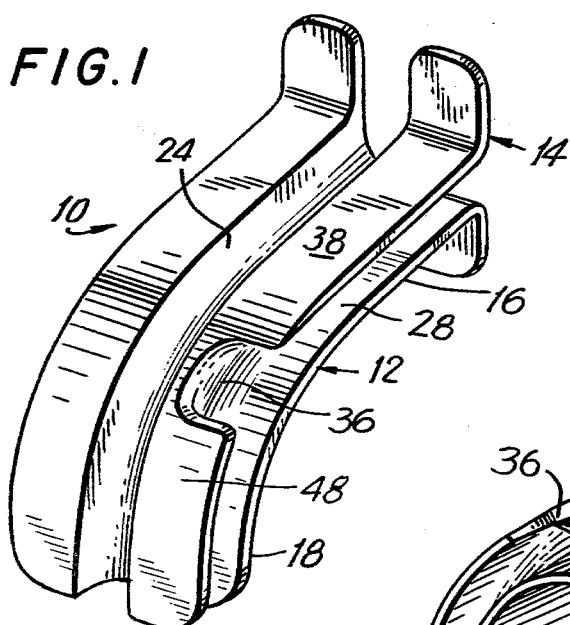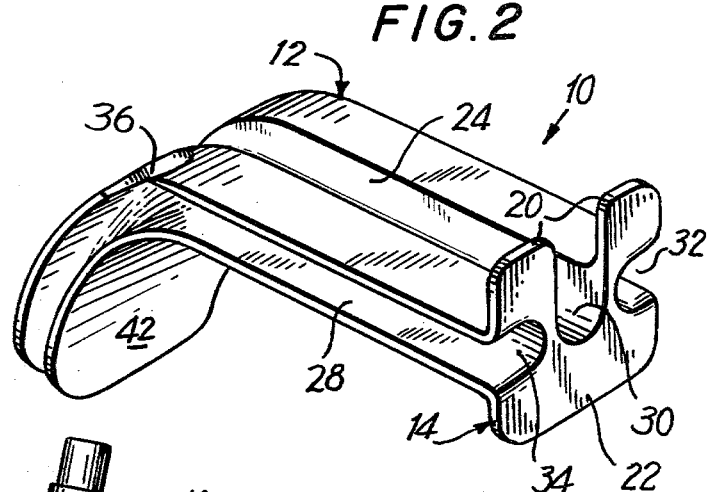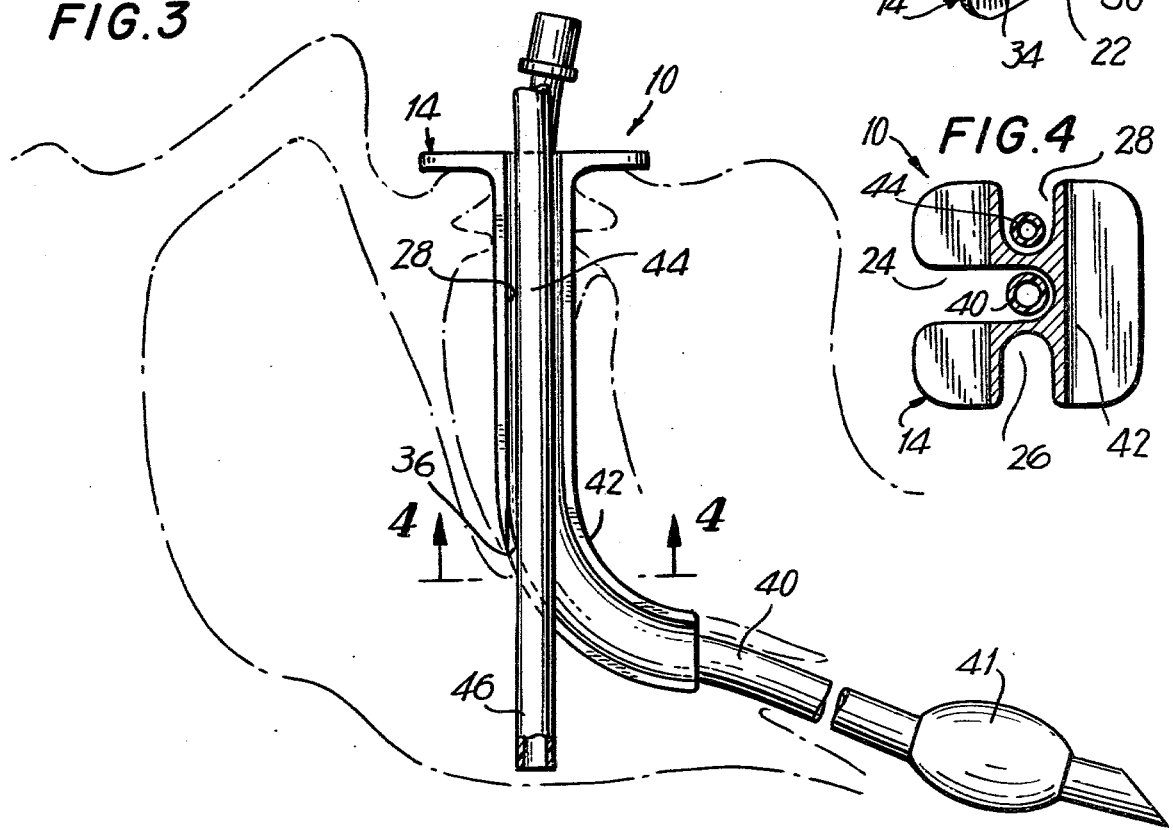

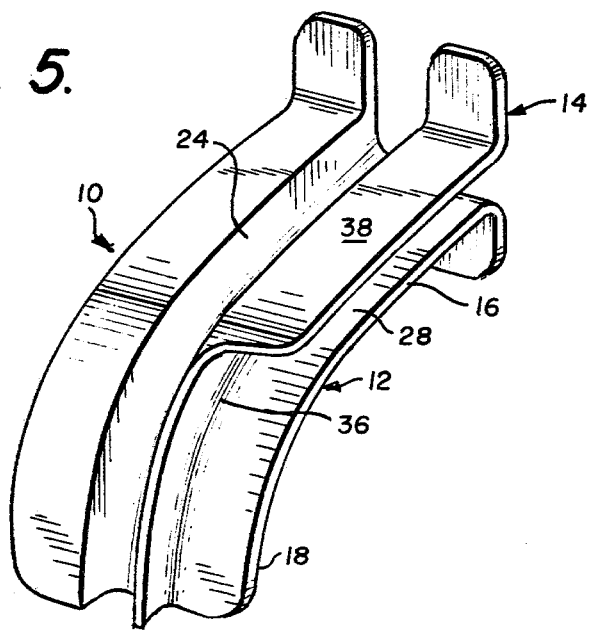

AIRWAY FOR DRAINAGE OF THE NASOPHARYNX

BACKGROUND OF THE INVENTION

1. Field of the Invention

This invention pertains generally to surgical appliances and more particularly to airways.

2. Statement of the Prior Art

Airways for use in endotracheal intubation are well known. See, e.g. U.S. Pat. Nos. 1,498,810, 2,599,521, 2,705,959, 3,306,298, 3,774,616, 3,908,665 and 4,054,135. Typically, they comprise an elongate body having a straight section and a curved section defining a longitudinally extending passageway, the curved section engaging and holding down the patient's tongue when the body of the airway is disposed in the patient's mouth. A face plate is generally secured to the straight section at its free end, the plate being engageable over the patient's mouth for holding the airway in place. The airway may be used by itself to provide an air passage between the lungs and mouth when, for example, a patient is unconscious as during surgery or from other causes such as severe head trauma. Generally, however, the airway is used in combination with an endotracheal tube either for breathing or administering anesthetics, oxygen, etc.

When using an airway, it is often necessary to extend a suction catheter into the patient's pharynx for removing accumulated phlegm, blood, saliva, etc. Accordingly, it is common as typified by U.S. Pat. Nos. 3,756,244 and 3,926,196, to provide multiple guides or channels in the airway for intubating both breathing tubes and suction catheters. Typically, a breathing tube will be inserted through a central guide or channel and the suction tubes intubated through side channels.

As noted above, the curved section of the airway is necessary to engage and hold down the patient's tongue. The curved section conforms to the curvature of the throat and thus also serves to properly guide and seat the endotracheal tube which is also curved. Accordingly, it is necessary that the airway be a sufficient length so that this function may be achieved. The design of prior art airways has been such that the suction catheters are guided the full length of the airway for suctioning the lower portion of the pharynx, known as the hypopharynx. Prior art airways are, therefore, not suited for suctioning the upper portion of the pharynx, known as the nasopharynx, in which the airway is situated. Accordingly, the use of prior art airways is typically accompanied by the accumulation of secretions in the nasopharynx which can result in patient discomfort and illness. If these secretions flow down the pharynx and occlude the endotracheal tube, breathing may also be restricted.

SUMMARY OF THE INVENTION

According to the invention, I have developed an airway which is capable of supporting the endotracheal tube in the midline of the throat while simultaneously suctioning fluids collecting in both the hypopharynx and the nasopharynx, which airway is nevertheless simple and inexpensive. The airway according to the invention comprises an elongate body having a straight section joined to a curved section and a face plate joined to the straight section at its free end. The body has an elongate U-shaped central channel open at the top and a pair of elongate open-sided U-shaped channels on either side of the central channel, the channels communicating with apertures in the face plate for receiving and supporting tubular members seated therein. The upper defining wall of one of the open-sided channels is provided with an opening, preferably substantially at the point where the straight section of the airway body is joined to the curved section. With the airway in place, this permits a conventional suction catheter to be intubated through the face plate into this channel and through the opening such that the distal end of the catheter terminates in the nasopharynx thus permitting suctioning of phlegm, sputum, blood, etc. therefrom. Suctioning of fluid accumulating in the hypopharynx may be effected by guiding a second suction catheter through the other side channel until the distal end thereof is situated in the hypopharynx beyond the end of the airway. When both the side channels are used for suctioning, the central channel will, of course, be used for breathing or administering oxygen, anesthetics, etc., preferably with the assistance of an endotracheal tube. Because the endotracheal tube is maintained in the midline of the throat by seating in the central channel, it need not be taped to one side of the mouth and will not press on the vocal chords or the larynx. Other instruments, such as a flexible bronchoscope, may be intubated in the endotracheal tube and like the tube will be maintained in the midline of the throat. This avoids the necessity of moving the bronchoscope from side to side to accommodate viewing different locations as is the case when the endotracheal tube and bronchoscope are taped to one side of the mouth.

Further features and advantages of the airway according to the present invention will become more fully apparent from the following detailed description and annexed drawing of the preferred embodiment thereof.

BRIEF DESCRIPTION OF THE DRAWING

In the drawing:

FIG. 1 is a perspective view of the preferred airway according to the present invention;

FIG. 2 is a different perspective view of the preferred airway according to the present invention;

FIG. 3 is an elevational view of the airway in situ;

FIG. 4 is a sectional view of the airway taken substantially along the lines 4—4 in FIG. 3; and FIG. 5 is a perspective view of a modified airway in accordance with the present invention.

DETAILED DESCRIPTION OF THE PREFERRED EMBODIMENT

Referring now to the drawings and initially to FIGS. 1, 2 and 4 thereof, the preferred airway 10 in accordance with the present invention is shown. As illustrated, airway 10 includes an elongate body 12 and a face plate 14, the body 12 having a preferably straight section 16 joined to a curved section 18. The face plate 14 preferably comprises upper and lower flanges 20 and 22 joined to straight section 16 at its free end.

The body 12 is provided with a preferably continuous longitudinally extending centrally located U-shaped channel 24 open at the top and a pair of preferably continuously extending open-sided U-shaped channels 26 and 28 on either side of said central channel 24. Face plate 14 is provided with apertures 30, 32 and 34 communicating with channels 24, 26 and 28, respectively, for accommodating intubation as will be more fully described hereinafter. As best shown in FIG. 1, an opening 36 is provided in the upper defining wall of one of the open-sided U-shaped channels, here shown to be the upper defining wall 38 of the channel 28. As presently preferred and shown, the opening 36 is provided in the portion of the wall 38 substantially at the juncture of straight section 16 with curved section 18. The reason for this will be more fully apparent hereinafter.

Those skilled in the art will appreciate that the airway 10 can be constructed from a variety of different materials and in a variety of different ways, all of which are acceptable for purposes of this invention. For example, if a reusable airway is contemplated, the airway will preferably be comprised of a suitable metal, such as aluminum, or a metal alloy. On the other hand, if, as is presently preferred, it is intended that the airway 10 be expendable, it is preferably injection molded from rubber or plastic. For example, a medical grade, non-allergenic ethylene vinyl acetate or polyethylene plastic may be used. Although an integral construction is preferred, this is not necessary. Thus, for example, the face plate 14 and the straight 16 and curved 18 sections of the body 12 may be separately formed and joined together thereafter. Whatever method of construction is employed, it is desirable that the edges be rounded and all surfaces be smoothed to avoid discomfort and possible damage upon insertion of the airway 10 in the patient's mouth and pharynx. It is contemplated that the actual dimensions of the airway 10 will vary to accommodate use with children and adults of varying sizes. Since some persons require larger endotracheal tubes than others, it is contemplated that some versions may have a wider central channel and shallower side channels than others.

With reference now to FIG. 3, in use, the airway 10 will most commonly be employed to secure an already intubated endotracheal tube 40 in place. The endotracheal tube 40 may be selectively positioned with the aid of an laryngoscope in a manner well known to those skilled in the art, the inflatable balloon 41 serving to hold the lower portion of the tube in the midline of the throat. With the endotracheal tube in place, the airway 10 is inserted into the patient's mouth such that the tube 40 seats in the central channel 24. Preferably, the width of the channel 24 will be slightly wider than the diameter of the endotracheal tube 40 so that the tube 40 may be seated in the channel 24 without difficulty. When the airway 10 is fully inserted into the patient's mouth, the face plate 14 comprised of the flanges 20 and 22 will engage the upper and lower lips, respectively, of the patient, the face plate 14 serving to prevent accidental inward displacement of the airway 10 into the patient's mouth during use. As shown in FIG. 3, when the airway 10 is in place, the distal end of the airway terminates in the hypopharynx and the lower defining wall 42 thereof engages and holds down the patient's tongue to prevent the tongue from slipping into the patient's throat.

When an airway is used, it is not uncommon for phlegm, saliva or even blood to accumulate in the patient's pharynx. Such fluid accumulation is likely to occur not only in the hypopharynx but also in the nasopharynx in which the curved section 18 of the body 12 is situated. When this happens, it is desirable to suction the nasopharynx before fluids accumulating therein flow down into the hypopharynx, which is likely to occur when a patient is on his back as during surgery. As will now be explained, the airway 10 of the present invention accommodates suctioning from both of these areas.

Referring to FIGS. 3 and 4, if suctioning of fluids collecting in the nasopharynx is desired, a suction catheter 44 may be intubated through the aperture 32 in the face plate 14 into the channel 26. As shown, it is desirable that the diameter of the tube 44 be considerably less than the width of the channel 26 to facilitate intubation and extubation of tube 44. It will be apparent that by applying slight downward pressure on the suction catheter 44 as it is fed into the channel 26, the distal end 46 of the catheter 44 will slide along the interior surface of the upper defining wall 38 of the channel 26. It will therefore be apparent that when the catheter 44 is intubated to the point where its distal end 46 confronts the opening 36, the end 46 will be guided through the opening 36 to, for example, the position shown in FIG. 3. Guiding of the catheter 44 through the opening 36 is facilitated if, as shown, the opening 36 is substantially at the juncture of curved section 16 and straight section 18. At this point, a conventional suction device (not shown) may be secured to the proximal end of the catheter 44 for suctioning fluids out of the nasopharynx through the catheter 44.

If it is desired to simultaneously suction fluids collecting in the hypopharynx, an additional suction catheter (not shown) may be intubated through aperture 34 into side channel 28 until the distal end of the catheter extends beyond the distal end of the airway 10. Once again, the diameter of the catheter is preferably less than the width of the channel 28. By using a conventional suction device in the manner described above, the fluids collecting in the hypopharynx may then be suctioned. Alternatively, the channel 28 may be used for intubation of other instruments as desired. Removal of the airway 10 is easily accomplished by first extubating the suction catheters and then removing the airway 10 and endotracheal tube 40.

It will be apparent from the above that the airway 10 is capable of effecting removal of accumulating fluids from both the hypopharynx and the nasopharynx. In addition, the airway 10 is simple, relatively inexpensive and suitable for integral construction as, for example, by injection molding from plastic. As such, it is ideally suited for emergency use for simply holding down the tongue of an unconscious patient or for breathing and suctioning as well.

While the use of the airway 10 has been described solely in connection with an endotracheal tube, it will be apparent that it may be used in other procedures as, for example, flexible bronchoscopy. In such case, the bronchoscope will be inserted in the endotracheal tube, and like the tube will be maintained in the midline of the patient's throat. Since the bronchoscope is of lesser diameter than the endotracheal tube 40, the patient can breathe through the portion of the tube 40 unobstructed by the bronchoscope thus allowing suctioning through channels 26 and 28 as is more fully described above.

Although the preferred airway 10 has been described, and methods of use suggested, it will be appreciated that changes and modifications may be made therein without departing from the spirit and scope of the invention. For example, while the aperture 36 is preferably located substantially at the juncture of the straight section 16 and curved section 18 of the body 12, this is not necessary, and other locations of the aperture 36 are possible. Also, if the channel 28 is to be used exclusively for suctioning the nasopharynx, the distal portion 48 of the upper defining wall 38 of the channel 26 may be eliminated (FIG. 5). However, this is not preferred as it would result in the elimination of the lower defining edge of the opening 36 upon which the catheter 44 rests when it is intubated in the nasopharynx. Furthermore, while the channel 24 has been described as centrally located, the term "centrally located" is not intended as one of precision and it should be understood that locations off center are also contemplated. Similarly, while the face plate 14 illustrated in the drawing is preferred, other face plate designs and constructions are acceptable. Also, while it is preferred and shown that the side walls defining the central channel 24 extend the full length of the airway 10, this too is not absolutely necessary.

Since these as well as other modifications and changes are intended to be within the scope of the present invention, the above description should be construed as illustrative and not in the limiting sense, the scope of the invention being defined by the following claims.

What is claimed is:

1. An airway for insertion into the mouth and pharynx of a patient comprising:

an elongated body including a straight section joined at one end to a curved section extending downwardly from said straight section, said body having an elongate U-shaped central channel having an open top, and a pair of elongate open-sided U-shaped channels on either side of the central channel, said open-sided U-shaped channels having upper and lower defining walls, the channels being adpated for receiving tubular members inserted therein;

a transverse plate secured to the other end of said straight section, the plate being engageable over the mouth of the patient and having apertures communicating with the channels; and the upper defining wall of one of the open-sided channels having a tube receiving opening therein disposed substantially at the juncture of said straight section with said curved section for receiving and guiding a tubular member inserted through said one channel into the nasopharynx for facilitating drainage thereof when said airway is in place.

2. The airway according to claim 1, wherein said opening extends from said juncture to the end of said body opposite said transverse plate.

3. The airway according to claim 1, wherein said body and said transverse plate are integral.

* * * * *